United States Patent [19]

Holloway

[11] Patent Number: 4,530,352

[45] Date of Patent: Jul. 23, 1985

[54] METHOD FOR APPLYING A SPLINT

[76] Inventor: Kenneth A. Holloway, 30904 Barton, Garden City, Mich. 48153

[21] Appl. No.: 547,564

[22] Filed: Nov. 1, 1983

[51] Int. Cl.³ .............................................. A61F 5/04
[52] U.S. Cl. .......................... 128/89 R; 128/DIG. 20
[58] Field of Search .................... 128/89 R, 90, 87 R, 128/DIG. 20

[56] References Cited

U.S. PATENT DOCUMENTS

| | | | |
|---|---|---|---|
| 3,110,307 | 11/1963 | Hamilton | 128/89 R |
| 3,674,021 | 7/1972 | Snyder et al. | 128/90 |
| 3,760,056 | 9/1973 | Rudy | 128/90 |
| 3,930,496 | 1/1976 | Gibbons | 128/DIG. 20 |
| 4,169,467 | 10/1979 | Rabischong et al. | 128/89 R |

FOREIGN PATENT DOCUMENTS 2041758  9/1980  United Kingdom ................. 128/90

*Primary Examiner*—John D. Yasko
*Attorney, Agent, or Firm*—Charles W. Chandler

[57] ABSTRACT

A method is disclosed for applying a splint to an injured body part in which a plurality of hollow, resilient tubes have their ends connected to a pair of spaced collars. A quick setting epoxy material is introduced into each tube in such a manner that when the epoxy hardens, the tubes cooperate to form a rigid splinting assembly about the injured body part.

6 Claims, 7 Drawing Figures

METHOD FOR APPLYING A SPLINT

BACKGROUND OF THE INVENTION

Conventionally, injured body parts, such as broken bones, are supported during the healing process by a cast, usually made of plaster of Paris. A conventional plaster of Paris cast is relatively unsanitary because it is difficult for the user to clean the skin area enclosed by the cast. Some splint devices have been disclosed in the prior art to permit the surface skin to be ventilated such as illustrated in U.S. Pat. No. 3,976,062, which issued Aug. 24, 1976, to Mervyn K. Cox.

SUMMARY OF THE INVENTION

The broad purpose of the present invention is to provide an improved splint assembly that can be readily assembled to form a ventilated support for an injured body part, and adapted to the curvature of the body parts, whether it be an arm, a leg or the like.

The preferred embodiment of the invention comprises two or more collars that are mounted around the injured body part such as a person's leg. Each collar has a series of parallel openings supported around the leg. A series of hollow tubes, formed of a non-toxic plastic, have their ends received in the collar openings. A plug is mounted in the bottom of each tube. The tubes are relatively flexible and tape is temporarily wrapped around the tubes so that they engage the leg surface with the desired pressure. A quick setting epoxy material is then introduced into the upper end of each tube to fill it. As the epoxy hardens, each hollow tube forms a rigid splint member with the tubes cooperating to form a rigid support about the injured body part. The tubes are separated sufficiently to permit ventilation of the major portion of the skin area supported by the splint.

Other embodiments employ collars adapted to be mounted on either the hand or foot to accommodate a wrist or ankle splint assembly.

The preferred method employs inexpensive modern materials and can be readily and quickly mounted in position to assist an injured person.

Still further objects and advantages of the invention will become readily apparent to those skilled in the art to which the invention pertains upon reference to the following detailed description.

DESCRIPTION OF THE DRAWINGS

The description refers to the accompanying drawings in which like reference characters refer to like part throughout the several views, and in which.

DESCRIPTION OF THE PREFERRED EMBODIMENT

Figure 1:
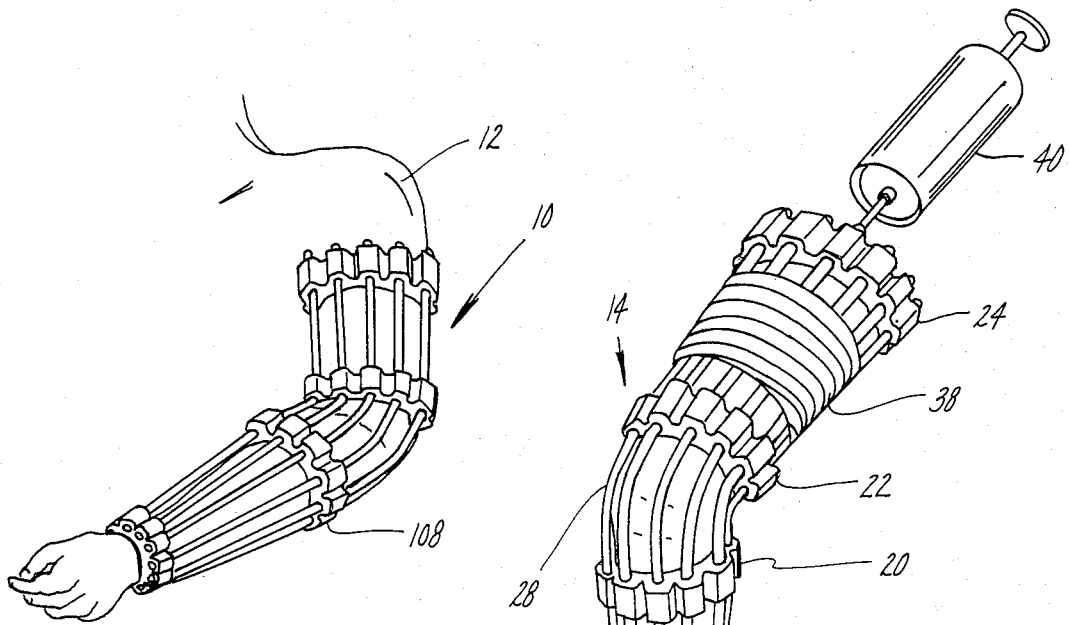
FIG. 1 is a perspective view illustrating the splint assembly mounted on an injured arm in accordance with the preferred method.
Figure 2:
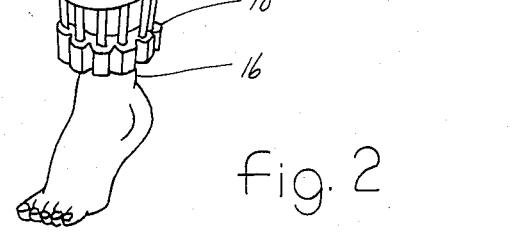
FIG. 2 illustrates another splint assembly mounted on an injured leg.

Referring to the drawings, splint means generally indicated at 10 are illustrated in FIG. 1 mounted on injured arm 12 of a user. Another splint assembly 14 is illustrated in FIG. 2 mounted on the injured leg 16 of a user. The method for mounting each assembly is identical varying only in the dimensions of the particular body part being braced.

Figure 3:
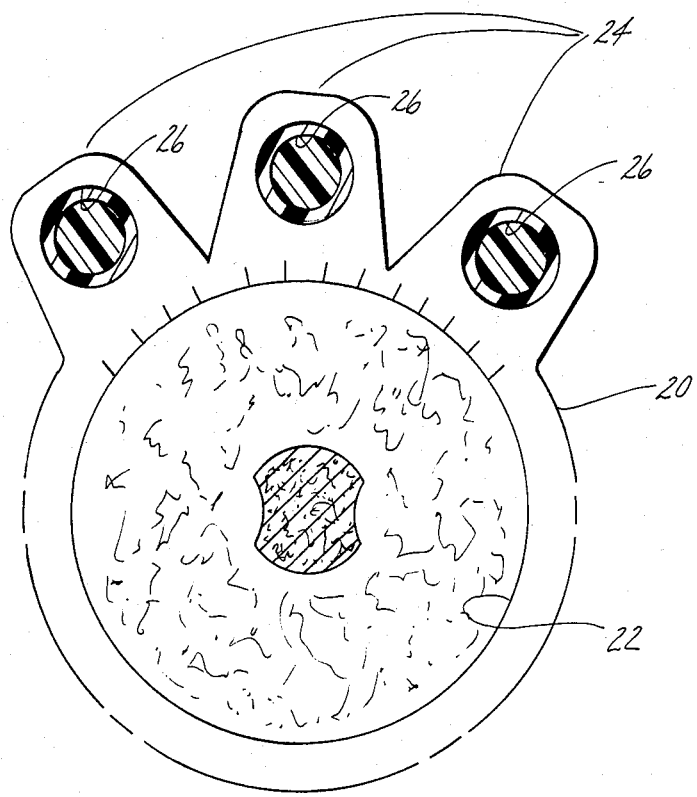
FIG. 3 is a view illustration a typical collar.

Referring to FIG. 2, four collars 18, 20, 22, and 24 are mounted on the user's leg. Each collar has a cross section as illustrated in FIG. 3, and is preferrably formed of a urathene material so as to be somewhat resilient. Preferrably, it is unrolled from a roll to form a strap having a length accommodating the diameter of the particular leg area. Collar 20 has a continuous inner band 22 and a series of spaced ridges 24. Each ridge 24 has an opening 26. The ridges can be separated to accommodate the curvature of the user's leg.

Figure 4:
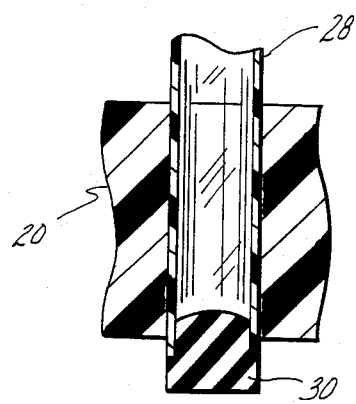
FIG. 4 is a view illustrating the manner in which a plug is mounted in the bottom of the tube.
Figure 5:
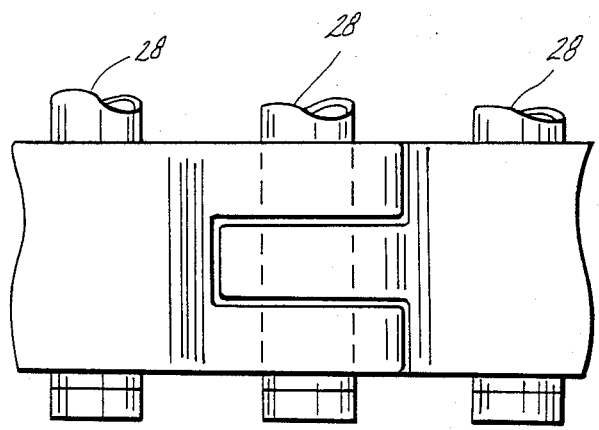
FIG. 5 illustrates the tongue and groove means for connecting the ends of a collar together.

A plurality of hollow tubes means 28 are received in openings 26. Preferably the tubing is unrolled from a roll of tubing formed of a non-toxic, clear plastic material, and then cut to length to accommodate the length of the injured body part. The tube means are mounted about the leg to expose the skin of the leg for ventilation. A typical tube 28 is illustrated in FIG. 4, received in collar 20. Plug 30 is inserted in the bottom end of each tube.

The user can remove the tube to separate the ends of the collar when the splint is to be removed from the injured part.

Referring to FIG. 2, when the tubes are mounted on the user's leg, the user then temporarily wraps tape 36 and 38 about the tubes so that they engage the skin area of the leg with the desired pressure. Each tube takes a shape accommodating the curvature of the particular leg area in which it is in contact.

When the leg is in the appropriate position and temporarily taped, the user delivers a liquid epoxy material from epoxy gun 40 into the upper end of each tube. Each tube is completely filled and then the leg held in the desired position until the epoxy hardens so that each tube forms a rigid splint member. Tape 36 and 38 is then removed to expose the skin area between the adjacent splint members. The splint assembly illustrated in FIG. 1 is formed in an identical manner.

Figure 6:
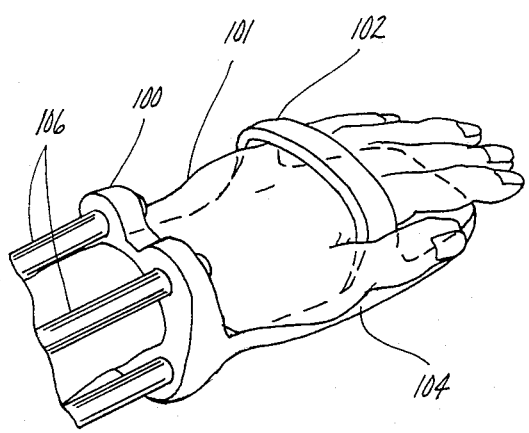
FIG. 6 illustrates a hand brace for supporting a series of tubes to form a wrist splint assembly.

FIG. 6 illustrates a collar 100 specifically adapted for forming a wrist splint assembly for wrist 101. In this case a second collar 102 receives the user's hand to hold the fingers straight and is connected to collar 100 by palm structure 104. Collar 100 supports the ends of a plurality of hollow tube means 106 which have been filled with a quick setting epoxy to form a splint assembly. The opposite end of the tubes are thus supported by a collar identical to that of collar 108 illustrated in FIG. 1.

Figure 7:
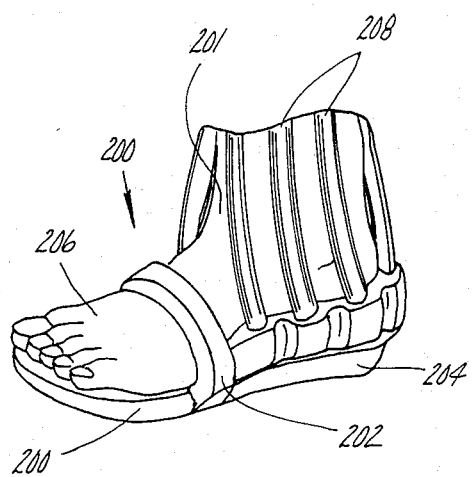
FIG. 7 illustrates a foot support for forming an ankle splint assembly.

Referring to FIG. 7, a splint assembly 200 supports ankle 201 and employs a collar 202 mounted on sole 204 adapted to support the user's foot 206. Collar 202 supports a plurality of tube means 208 which have received a quick setting epoxy to form a rigid splint assembly. The upper ends of the tube means are supported by a collar such as 20 illustrated in FIG. 2.

Thus it is to be understood that I have described an improved splint system for bracing an injured body part by employing a plurality of hollow, flexible tubes supported parallel to the injured body part. Each tube is filled with a quick setting epoxy of any suitable manufacture. When the epoxy hardens, the splint members cooperate to support and brace the injured body part. The splint system can be quickly and easily removed, and provides a brace that can be readily cleaned.

Having described my invention, I claim:

1. A method for applying a splint to brace an injured body part comprising:

mounting a pair of spaced collars along the injured body part, each collar having a plurality of openings for receiving a plurality of tubular splint members, each collar comprising an elongated strap, and tongue and groove means for connecting the ends of the strap together;

supporting a plurality of resiliant, tubular splint members adjacent and about the injured body part such that each tubular splint member is received in aligned openings in the spaced collars, one of the tubular splint members being received by the tongue and groove means to join the strap ends of the two collars together;

filling the tubular splint members with a liquid material capable of hardening to a solid state; and permitting the liquid material to harden such that the tubular splint members become rigid to brace the injured body part.

2. A method as defined in claim 1, in which the liquid material comprises an epoxy material.

3. A method as defined in claim 1, in which the body part has a generally longitudinal axis, and the tubular splint members are supported in a spaced relationship, generally parallel to the longitudinal axis of the body part, and including tape means for temporarily holding the tubular splint members against the injured body part until the liquid material hardens to a solid state.

4. A method as defined in claim 1, in which the body part includes a joint such that one end of the body part is disposed at an angle with respect to the other end of the body part, and in which the tubular splint members each have a bend disposed adjacent said joint.

5. A method as defined in claim 1 in which each tubular splint member has opposite open ends, and including plug means mounted in one end of each tubular splint member, the liquid material being receivable in the opposite end.

6. A method for applying a splint to brace an injured elongated body part, comprising the steps of:

supporting a plurality of resiliant tubular splint members adjacent and about the injured body part in a spaced relationship parallel to the longitudinal axis of the injured body part;

the hollow splint members each having an opening;

mounting at least a pair of spaced collars along the injured body part, each collar having opening means for receiving each of the hollow splint members so as to support the ends thereof;

filling each of the hollow splint members through their respective opening with a liquid material capable of hardening to a solid state;

applying a tape about the midsection of the splint members to hold them against the injured body part until the liquid material hardens to a solid state such that the tubular splint members collectively brace the injured body part; and removing the tape material to permit ventilation of the skin disposed between the tubular splint members.

* * * * *